(12) United States Patent
Lack et al.

(10) Patent No.: US 10,067,045 B2
(45) Date of Patent: Sep. 4, 2018

(54) AMMONIA ESTIMATION METHOD

(71) Applicant: INTERNATIONAL ENGINE INTELLECTUAL PROPERTY COMPANY, LLC, Lisle, IL (US)

(72) Inventors: Adam C Lack, Boulder, CO (US); Navtej Singh, Arlington Heights, IL (US); Michael James Miller, Mt. Prospect, IL (US)

(73) Assignee: International Engine Intellectual Property Company, LLC., Lisle, IL (US)

( * ) Notice: Subject to any disclaimer, the term of this patent is extended or adjusted under 35 U.S.C. 154(b) by 510 days.

(21) Appl. No.: 14/440,279

(22) PCT Filed: May 28, 2013

(86) PCT No.: PCT/US2013/042830
§ 371 (c)(1),
(2) Date: May 1, 2015

(87) PCT Pub. No.: WO2014/070247
PCT Pub. Date: May 8, 2014

(65) Prior Publication Data
US 2015/0300934 A1    Oct. 22, 2015

Related U.S. Application Data

(60) Provisional application No. 61/722,130, filed on Nov. 2, 2012.

(51) Int. Cl.
*G01N 7/16* (2006.01)
*F01N 3/20* (2006.01)
*F01N 11/00* (2006.01)

(52) U.S. Cl.
CPC ............ *G01N 7/16* (2013.01); *F01N 3/2066* (2013.01); *F01N 11/00* (2013.01);
(Continued)

(58) Field of Classification Search
CPC ......... G01N 7/16; F01N 3/2066; F01N 11/00; F01N 2610/02; F01N 2610/06; F01N 2900/1808
(Continued)

(56) References Cited

U.S. PATENT DOCUMENTS

| 8,088,201 B2* | 1/2012 | Johannessen | ...... B01D 53/9431 |
| | | | 423/212 |
| 2010/0021780 A1* | 1/2010 | Johannessen | ...... B01D 53/8631 |
| | | | 429/421 |

(Continued)

*Primary Examiner* — Daniel S Larkin
(74) *Attorney, Agent, or Firm* — Jeffrey P. Calfa; Jack D. Nimx

(57) ABSTRACT

A method for determining the degree of saturation of a solid ammonia storage material in a storage unit includes activating a heater to release ammonia from the storage material until the pressure of the storage unit reaches a predetermined pressure. The method then deactivates the heater and determining a decay rate of the pressure of the storage unit while the heater is deactivated. The method estimates the degree of saturation of the ammonia storage medium in response to the decay rate. According to some embodiments, determining the decay rate may include measuring the time required for the pressure of the storage unit to drop from a first pressure threshold to a second pressure threshold.

10 Claims, 3 Drawing Sheets

(52) U.S. Cl.
CPC ...... *F01N 2610/02* (2013.01); *F01N 2610/06* (2013.01); *F01N 2900/1808* (2013.01); *Y02T 10/24* (2013.01); *Y02T 10/47* (2013.01)

(58) Field of Classification Search
USPC ........................................................ 73/19.05
See application file for complete search history.

(56) References Cited

U.S. PATENT DOCUMENTS

| | | | | |
|---|---|---|---|---|
| 2012/0072135 A1* | 3/2012 | Quaade | ................... | C01C 1/006 702/55 |
| 2013/0209316 A1* | 8/2013 | Johannessen | ........... | C01C 1/006 422/109 |

\* cited by examiner

AMMONIA ESTIMATION METHOD

BACKGROUND

Selective catalytic reduction (SCR) is commonly used to remove $NO_x$ (i.e., oxides of nitrogen) from the exhaust gas produced by internal engines, such as diesel or other lean burn (gasoline) engines. In such systems, $NO_x$ is continuously removed from the exhaust gas by injection of a reductant into the exhaust gas prior to entering an SCR catalyst capable of achieving a high conversion of $NO_x$.

Ammonia is often used as the reductant in SCR systems. The ammonia is introduced into the exhaust gas by controlled injection either of gaseous ammonia, aqueous ammonia or indirectly as urea dissolved in water. The SCR catalyst positioned in the exhaust gas stream causes a reaction between $NO_x$ present in the exhaust gas and a $NO_x$ reducing agent (e.g., ammonia) to reduce/convert the $NO_x$ into nitrogen and water.

In many applications, such as SCR systems for vehicles, for example, the storage of ammonia in the form of a pressurized liquid in a vessel may be too hazardous and a storage method involving absorption in a solid may circumvent the safety hazard of anhydrous liquid ammonia. For example, metal ammine salts are ammonia absorbing materials, which can be used as solid storage media for ammonia, which in turn, for example, may be used as the reductant in SCR to reduce $NO_x$ emissions from internal combustion engines in vehicles, see e.g., U.S. Pat. No. 8,088,201 and WO 1999/01205. The ammonia can be released from the ammine salts through thermal desorption, e.g., by external heating of a storage container, see e.g., id. and U.S. Patent App. Pub. No. 2010/0086467. The ammonia is released from an either adsorptive or absorptive solid storage medium, among others $Sr(NH_3)_8Cl_2$ or $Ca(NH_3)Cl_2$ in granular form, in a storage container and temporarily stored as a gas in a buffer volume. The amount of ammonia to be supplied to a reaction volume in the vehicle's exhaust system is dosed under the control of an electronic controller according to the current operating state of the engine.

The ammonia is consumed during driving, and as a result, the storage medium is depleted over time. Eventually, the ammonia in a canister is depleted and must be recharged or replaced. Replacing the canisters too early is obviously undesirable, as it can result in increased cost and vehicle down time, for example. Conversely, if the user waits too long to recharge or replace the canister, the SCR system may stop functioning correctly, causing undesirable NOx emissions. Accordingly, it is desirable to be able to determine the fill level of the storage container and to alert the user when the canister is nearing depletion.

SUMMARY

Aspects and embodiments of the present technology described herein relate to one or more systems and methods for estimating the saturation level of a solid ammonia storage medium.

At least some embodiments of the present technology relate to a method for determining the degree of saturation of a reversible solid ammonia storage material in a storage unit. The storage unit being equipped with a heater to release ammonia. The method includes monitoring the pressure of the storage unit and detecting deactivation of the heater. Upon detecting deactivation of the heater, the method measures the time required for the pressure of the storage unit to drop from a first pressure threshold P1 to a second pressure threshold P2. The method then estimates the degree of saturation ammonia storage medium in response to the measured time.

In some embodiments, the estimating step includes accessing a look-up table that correlates the measured time to a degree of saturation.

According to at least some embodiments, the method may further indicate a saturation level in response to the estimated saturation level.

In accordance with certain other aspects of at least one embodiment of the present technology, a method for determining the degree of saturation of a solid ammonia storage material in a storage unit includes activating a heater to release ammonia from the storage material until the pressure of the storage unit reaches a predetermined pressure. The method then deactivates the heater and determines a decay rate of the pressure of the storage unit while the heater is deactivated. The method estimates the degree of saturation of the ammonia storage medium in response to the decay rate. According to some embodiments, determining the decay rate may include measuring the time required for the pressure of the storage unit to drop from a first pressure threshold P1 to a second pressure threshold P2.

One or more embodiments of the present technology relate to a system for determining the degree of saturation of a solid ammonia storage material in a storage unit. The storage unit includes a heater to release ammonia from the storage material. The system includes a pressure sensor and a controller. The pressure sensor senses the internal pressure of the storage unit and produces a pressure signal responsive thereto. The controller is configured to monitor the pressure signal and selectively activate the heater to release ammonia until the pressure of the storage unit reaches a predetermined pressure. The controller is also configured to deactivate the heater to allow the pressure in the storage unit to decay, determine a decay rate of the pressure of the storage unit, and determine the degree of saturation of the ammonia storage medium in response to the determined decay rate. In some embodiments, the controller determines the decay rate by measuring the time required for the pressure signal to drop from a first pressure threshold P1 to a second pressure threshold P2.

DETAILED DESCRIPTION

Various examples of embodiments of the present technology will be described more fully hereinafter with reference to the accompanying drawings, in which such examples of embodiments are shown. Like reference numbers refer to like elements throughout. Other embodiments of the presently described technology may, however, be in many different forms and are not limited solely to the embodiments set forth herein. Rather, these embodiments are examples representative of the present technology. Rights based on this disclosure have the full scope indicated by the claims.

Figure 1:
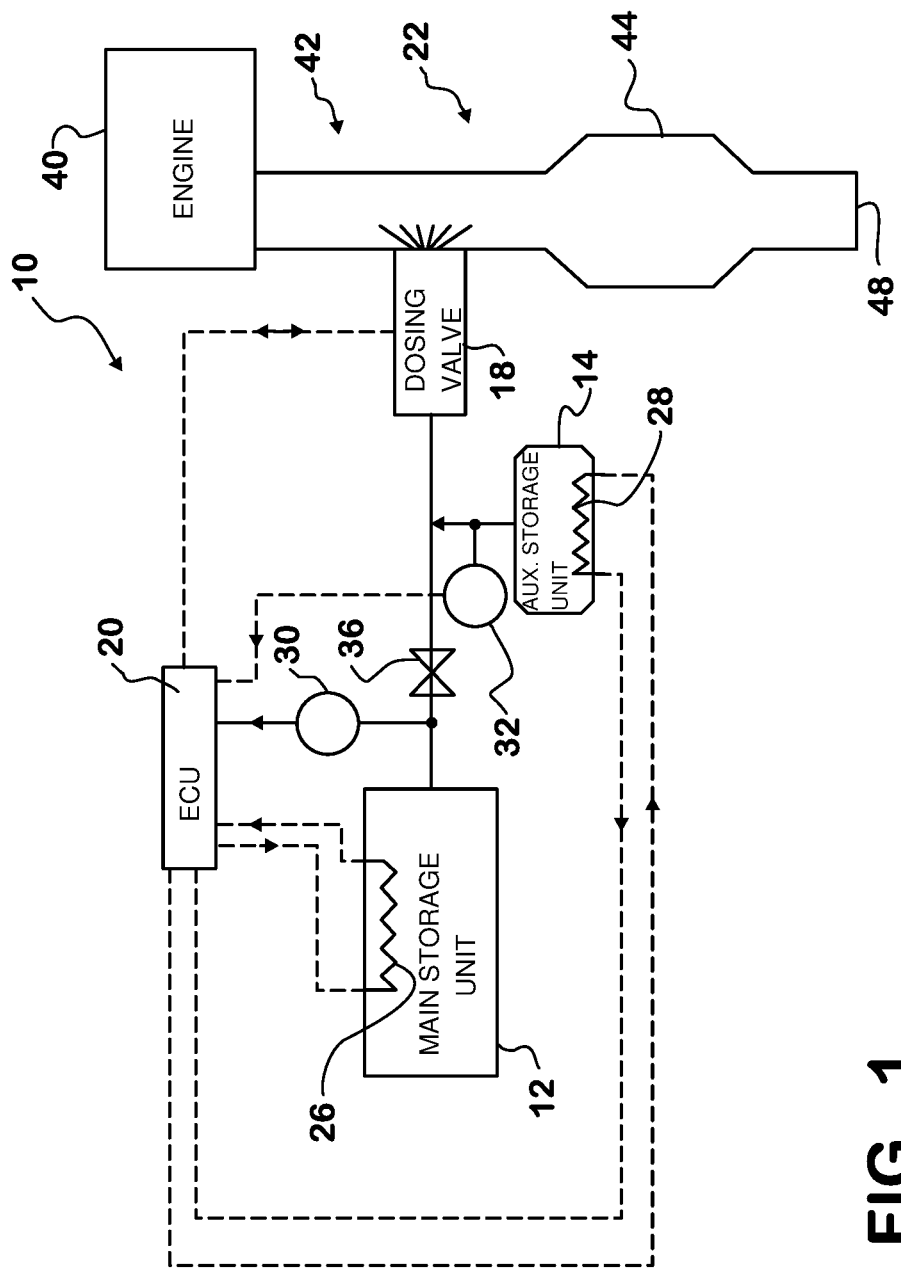
FIG. 1 is a schematic illustration of an exemplary ammonia storage and dosing system that can be used to implement at least one embodiment of the present technology.

FIG. 1 is a schematic diagram illustrating an embodiment of an exemplary ammonia storage and dosing system 10. In the illustrated embodiment, the ammonia storage and dosing system 10 includes a main storage unit 12 and a start-up storage unit 14. In the example of FIG. 1, the main storage unit 12 is made up of a single storage container, which holds ammonia storage material. It will be appreciated, however, that the storage material of the main storage unit 12 can be held in more than one container. The start-up storage unit 14 can be relatively small compared to the main storage unit 12, to facilitate rapid start-up. The number and the size of the other containers that make up the main storage unit 12 can vary in accordance with design and performance parameters, including, for example, the desired total ammonia amount reserves and the start-up time of the main storage unit. The coupling of several storage containers can be performed in a variety of different ways in combination with passive one-way valves, active valves, pressure sensors, pressure switches, etc. Additional details and considerations regarding the size and number of storage units are provided in U.S. Patent Application Pub. No. 2010/0086467 (the "467 Publication"), the disclosure of which is hereby incorporated in its entirety.

The storage units 12, 14 are fluidly connected to a dosing valve 18 by which ammonia from the storage units 12, 14 is dosed according to a demand to an ammonia consuming process or system 22, such as a selective catalytic reduction (SCR) system. An electronic control unit 20 controls operation of the dosing valve 18 to control delivery of ammonia from the storage and dosing system 10 to the consuming system 22.

Pressure sensors 30, 32 monitor the pressure in the main and start-up storage units 12, 14, respectively and produce signals indicative of the sensed pressures. The ECU 20 is coupled to the pressure sensors 30, 32 for receipt of the pressure signals.

Heating units 26, 28, such as electrical heaters, are provided for heating the main storage unit 12 and the start-up storage unit 14, respectively. The heating units 26, 28 can be placed inside the main storage unit 12 and the start-up storage unit 14 containers, respectively.

The ECU 20 is operable to control (e.g., switch on or off, and/or regulate) the heating units 26, 28 independently from each other, e.g., by controlling the power supplied to them. The ECU 20 can be programmed to regulate operation of the start-up heating unit 28 to initially raise pressure $P_S$ in the start-up storage unit 14 to its activation pressure. Once the activation pressure of the start-up storage unit 14 is reached, the start-up heating unit 28 is modulated on and off to maintain pressure $P_S$ in the start-up storage unit 14 at or about its activation. When the start-up heating unit 28 is cycled off, the main heating unit 26 is cycled on to gradually raise the pressure $P_M$ in the main storage unit 12 towards its activation pressure. During the start-up mode, the main and start-up heating units 26, 28 are modulated to maintain the start-up storage unit 14 around its activation pressure, while raising the pressure $P_M$ in the main storage unit 12 during the times that the start-up heating unit 28 is off. Accordingly, the pressure in the start-up heating unit 28 can be quickly raised to the activation pressure so that the system can begin supplying reductant from the start-up storage unit 14. Once the pressure $P_M$ in the main storage unit 12 reaches its activation pressure, the system/method transitions to the main mode where reductant is supplied from the main storage unit 12. During the main mode, the start-up heating unit 28 can remain inactive, while the main heating unit 26 is modulated on and off to maintain the pressure in the main storage unit 12 at or about its activation pressure. Because the heating units 26, 28 are never active at the same time, the power requirements, e.g., from a vehicle power system, can be reduced.

According to at least some embodiments, a valve can fluidly couple the main storage unit 12 and the start-up storage unit 14. In some embodiments, the valve can be a passive, one-way valve 36. The one-way valve 36 closes when the pressure downstream of it (i.e., the pressure in the start-up storage unit 14) is higher than that upstream of it (i.e. lower than the pressure in the main storage unit 12), and opens when the upstream pressure becomes higher than the down-stream pressure. Accordingly, the one-way valve 36 allows the main storage unit 12 to resaturate the smaller (rapid) start-up storage unit 14 with ammonia, e.g., in situations where the system 10 is powered off (because the pressure in the main storage unit 12 will be higher than that in the start-up storage unit 14, when the main storage unit 12 is more saturated), or where heating of the start-up storage unit 14 has ceased while the main storage unit 12 continues to be heated. This increases the likelihood that the smaller, start-up storage unit, is available to make a rapid start-up. At the same time, the one-way valve 36 prevents ammonia from being introduced into the main storage unit 12 from the smaller start-up storage unit 14 when the pressure in the latter is higher, particularly during start-up.

The ECU 20 is also configured to control the dosing valve 18, e.g., by providing the dosing valve with a variable dosing target value (for example, the dosing target value prescribes a certain degree of opening of the dosing valve). In the embodiment illustrated in FIG. 1, the ammonia storage and dosing system 10 is used to supply reductant (i.e., ammonia) for selective catalytic reduction (SCR) of $NO_x$ in the exhaust emitted by an internal combustion engine 40. The ECU 20 (or another controller) controls delivery of ammonia from the storage and dosing system 10 and into the exhaust system 42 through the dosing valve 18. The dosing valve 18 may be positioned in the exhaust system 42 upstream from a catalyst 44. As the ammonia is injected into the exhaust system 42, it mixes with the exhaust gas and this mixture flows through the catalyst 44. The catalyst 44 causes a reaction between $NO_x$ present in the exhaust gas and a $NO_x$ reducting agent (e.g., ammonia) to convert the $NO_x$ into nitrogen and water, which then passes out of a tailpipe 48 and into the environment. While the system 10 has been described in the context of SCR for engine exhaust, it will be appreciated that the system could be used to supply ammonia in other applications, such as ammonia used as an energy carrier for a fuel cell or ammonia used as a reactant or additive in a chemical reaction, as described in greater detail in the aforementioned 467 Publication.

Certain aspects of the present technology relate to a system for determining the degree of saturation of a solid ammonia storage material in a storage unit, such as the main storage unit 12 and/or the auxiliary storage unit 14. For illustration purposes, the system will be described in connection with the main storage unit 12. In order to determine the ammonia saturation level of the storage unit 12, the ECU 20 may initially activate the heating unit 26 to release ammonia from the solid ammonia storage material. The heating unit 26 may remain active, e.g., energized, until the pressure in the main storage unit reaches a predetermined pressure, such as the activation pressure of the main storage unit. As will be appreciated, this step can occur during normal operation ammonia storage and dosing system 10, such as upon power-up of the system 10, or may be performed as a part of a separate process for estimating the saturation level of the main storage unit 12.

Figure 2:
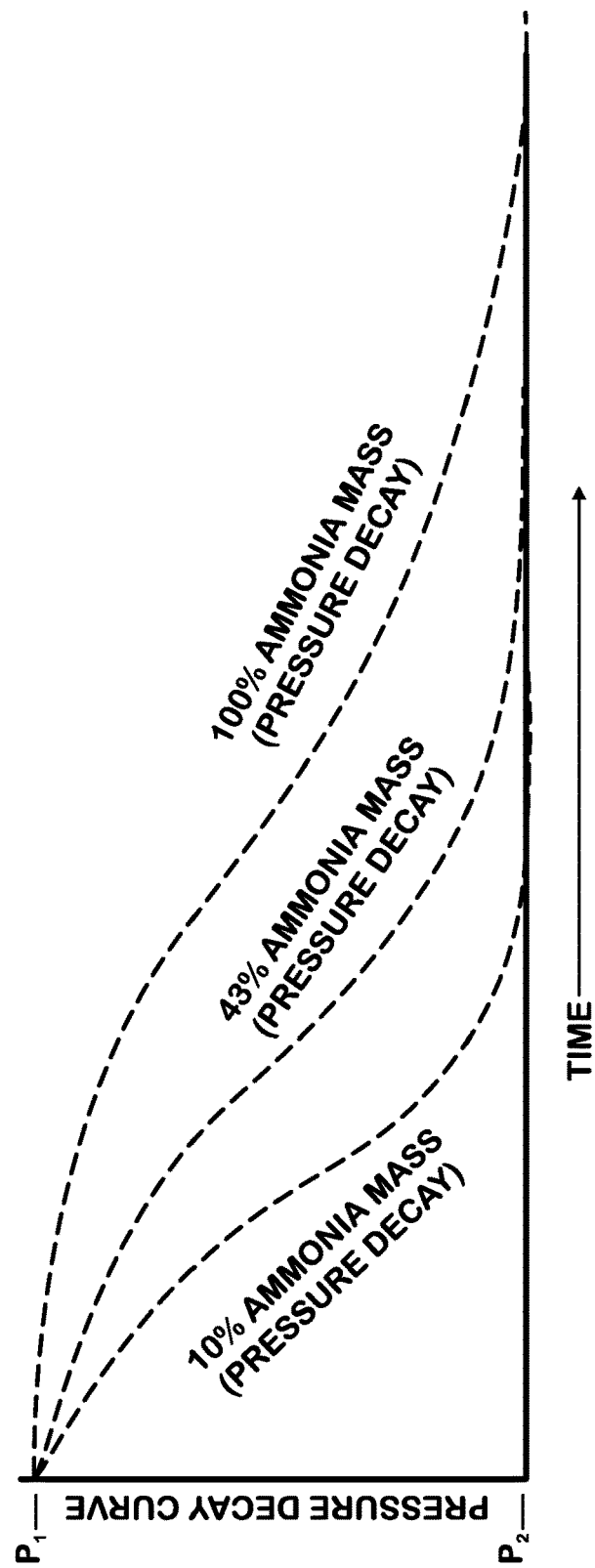
FIG. 2 is an exemplary graph illustrating the relationship between ammonia saturation level and pressure decay.

The ECU 20 monitors the pressure in the main storage unit 12 by monitoring the output of the pressure sensor 30. Once the pressure in the main storage unit 12 reaches the predetermined pressure the ECU 12 deactivates the heating unit 26. The ECU 20 continues to monitor the pressure signal while the heating unit is deactivated to determine a decay rate of the pressure of the storage unit. The ECU 20 is configured to determine the degree of saturation of the ammonia storage medium in response to the determined decay rate. In this regard, thermal inertia of the storage unit 12 will vary as a function of the saturation level of the storage unit. In particular, the thermal inertia of the storage unit will decrease as the storage unit becomes more empty, i.e., with decreasing saturation levels. This concept is illustrated in FIG. 2, which illustrates varying decay rates as a function of saturation level. As can be seen, the pressure decays more slowly from a full storage unit than from a storage unit that is only partially full. Accordingly, the pressure decay rate may be used to estimate the saturation level of the storage unit 12.

According to at least some embodiments, the ECU 20 may determine the decay rate by measuring the time required for the pressure signal to drop from a first pressure threshold P1 to a second pressure threshold P2. In some embodiments, the ECU 20 may determine saturation level by accessing a look-up table that correlates the measured time to a degree of saturation.

In some embodiments, the ECU 20 may be configured to provide an indication of the saturation level of the storage unit to a user. For example, the method may include controlling a display that provides an output indicative of the estimated saturation level to the user. Alternatively or additionally, the method may provide an alert when the estimated saturation level drops below a predetermined value, such as 10% of the maximum. The alert can take various forms, such as an audible and/or visual alert.

Figure 3:
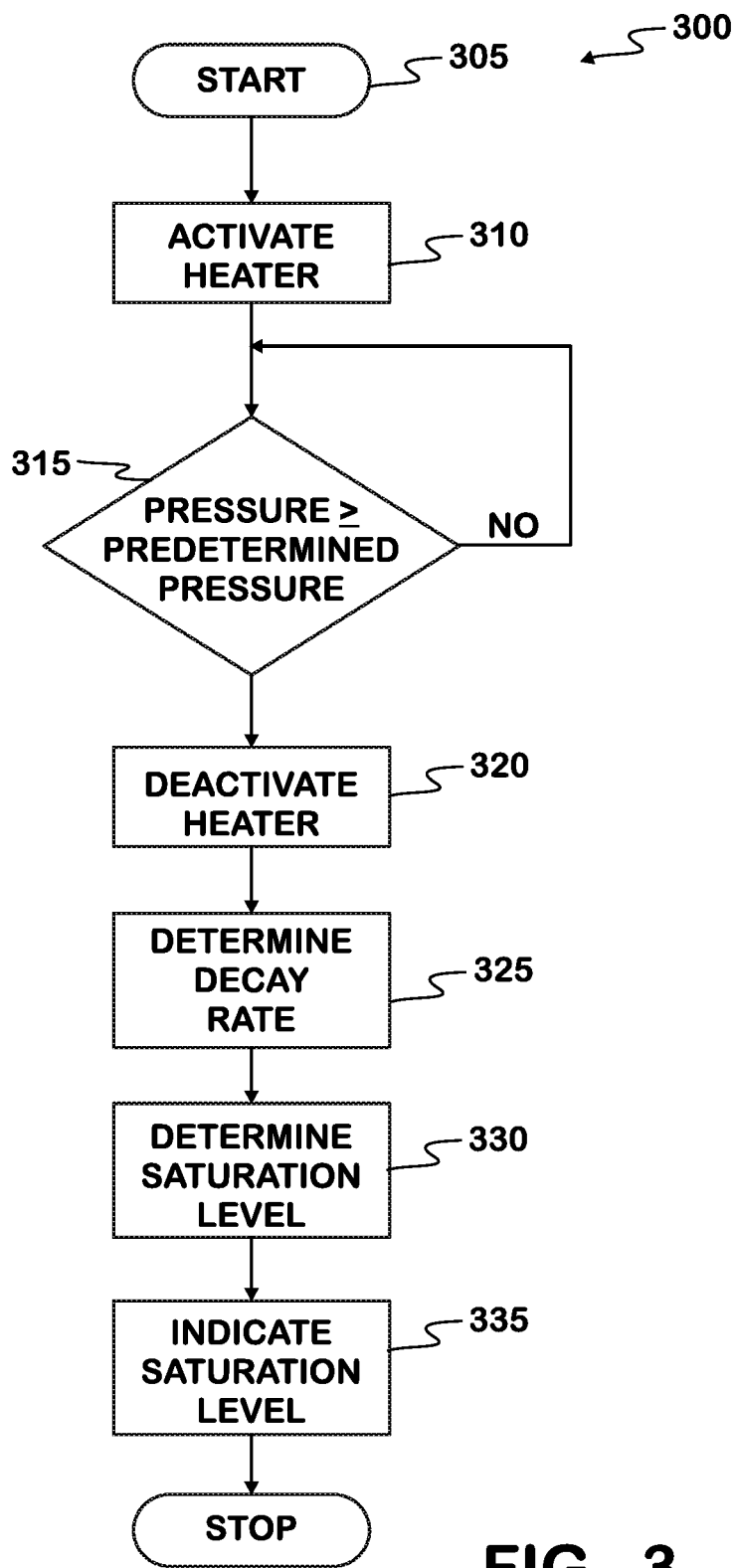
FIG. 3 is a flow diagram of an exemplary method for estimating the saturation level of a solid ammonia storage medium according to at least one embodiment of the present technology.

FIG. 3 is a flow chart illustrating at least one embodiment of a method 300 for estimating the saturation level of a solid ammonia storage medium according to at least one embodiment of the present technology. The method may be used, for example, to determine the saturation level of the main storage unit 12 and/or the start-up storage unit 14. For illustration purposes, the method will be described in connection with the main storage unit 12.

The method begins in step 305. Control is then passed to the step 310, where the method activates the heating unit 26 to release ammonia from the storage medium. The method continues to heat the main storage unit 12 until its pressure storage unit reaches a predetermined pressure. In this regard, the method continues to loop through step 315 until the pressure of the main storage unit 12 is at or above the predetermined pressure. Once the pressure in the storage unit reaches the predetermined pressure, control is passed to step 320, where the method deactivates the heating unit 26.

Control is then passed to step 325, where the method 300 determines a decay rate of the pressure of the storage unit 12 while the heater unit 26 is deactivated. In some embodiments, the decay rate may be determined by measuring the time required for the pressure of the storage unit to drop from a first pressure threshold P1 to a second pressure threshold P2.

Control is then passed to step 330, where the method 300 estimates the saturation level of the storage unit 12 based on the decay rate determined in step 325. According to at least some embodiments, the method 300 may determine the decay rate by measuring the time required for the pressure signal to drop from a first pressure threshold P1 to a second pressure threshold P2. In some embodiments, the method 300 may determine saturation level by accessing a look-up table that correlates the measured time to a degree of saturation.

In some embodiments, the method 300 may further include the step 335 of providing an indication of the saturation level of the storage unit to a user. For example, the method 300 may include controlling a display that provides an output indicative of the estimated saturation level to the user. Alternatively or additionally, the method 300 may provide an alert when the estimated saturation level drops below a predetermined value, such as 10% of the maximum. The alert can take various forms, such as an audible and/or visual alert.

In some embodiments, the method may be used to determine the saturation level following periods when the SCR system has been active, such as when the vehicle is turned off.

While this disclosure has been described as having exemplary embodiments, this application is intended to cover any variations, uses, or adaptations using the general principles set forth herein. It is envisioned that those skilled in the art may devise various modifications and equivalents without departing from the spirit and scope of the disclosure as recited in the following claims. Further, this application is intended to cover such departures from the present disclosure as come within the known or customary practice within the art to which it pertains.

The invention claimed is:

1. A method for determining the degree of saturation of a reversible solid ammonia storage material in a storage unit, the storage unit being equipped with a heater to release ammonia, the method comprising:
    monitoring the pressure of the storage unit;
    detecting deactivation of the heater;
    upon detecting deactivation of the heater, measuring the time required for the pressure of the storage unit to drop from a first pressure threshold to a second pressure threshold; and
    determining the degree of saturation ammonia storage medium in response to the measured time.

2. A method as set forth in claim 1, wherein the step of determining includes accessing a look-up table that correlates the measured time to a degree of saturation.

3. A method as set forth in claim 1, further comprising providing an indication of saturation level to a user in response to the determined saturation level.

4. A method for determining the degree of saturation of a solid ammonia storage material in a storage unit, the storage unit being equipped with a heater to release ammonia, the method comprising:
    activating the heater to release ammonia from the solid ammonia storage material until the pressure of the storage unit reaches a predetermined pressure;
    deactivating the heater;
    determining a decay rate of the pressure of the storage unit while the heater is deactivated; and
    determining the degree of saturation of the ammonia storage medium in response to the decay rate.

5. A method as set forth in claim 4, further comprising the step of monitoring the pressure of the storage unit.

6. A method as set forth in claim 4, wherein the step of determining a decay rate further comprises measuring the time required for the pressure of the storage unit to drop from a first pressure threshold to a second pressure threshold.

7. A system for determining the degree of saturation of a solid ammonia storage material in a storage unit, the storage unit being equipped with a heater to release ammonia, the system comprising:
  a sensor configured to sense the internal pressure of the storage unit and produce a pressure signal responsive thereto; and
  a controller configured to monitor the pressure signal, selectively activate the heater to release ammonia from the storage material until the pressure of the storage unit reaches a predetermined pressure, deactivate the heater to allow the pressure in the storage unit to decay, determine a decay rate of the pressure of the storage unit, and
  determine the degree of saturation of the ammonia storage medium in response to the determined decay rate.

8. A system as set forth in claim 7, wherein the controller determines the decay rate by measuring the time required for the pressure signal to drop from a first pressure threshold to a second pressure threshold.

9. A system as set forth in claim 7, further comprising a valve connected to the storage unit for controlling the release of ammonia from the storage unit and wherein the controller is further configured to control actuation of the valve.

10. A system as set forth in claim 9, wherein the sensor is interconnected between the storage unit and the valve.

* * * * *